US00PP11212P

United States Patent [19]

VandenBerg

[11] Patent Number: Plant 11,212

[45] Date of Patent: Feb. 8, 2000

[54] CHRYSANTHEMUM PLANT NAMED 'PURPLE YOLIMA'

[75] Inventor: Cornelis P. VandenBerg, Salinas, Calif.

[73] Assignee: Yoder Brothers, Inc., Barberton, Ohio

[21] Appl. No.: 09/112,332

[22] Filed: Jul. 9, 1998

[51] Int. Cl.[7] ..... A01H 5/00

[52] U.S. Cl. ..... Plt./286

[58] Field of Search ..... Plt./286, 297

[56] References Cited

U.S. PATENT DOCUMENTS 4,616,099 10/1986 Sparkes ..... 47/58

OTHER PUBLICATIONS

Broertjes, et al., 1980, A mutant of a mutant of a . . . Irradiation of progressive radiation–induced mutants in a mutation breeding programme with Chrystanthemum morifolium, Euphytica, 29:525–530.

Gosling, ed., 1979, The Chrysanthemum Manual—6$^{th}$ edition, The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrystanthemums The Year Round", Blanford Press, London, pp. 27–29, 320–327.

Chan, 1966, "Chrysanthemum and rose mutations induced by x–rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in Chrysanthemum using x–and gamma radiation", Euphytica, 15:204–210.

*Primary Examiner*—Howard J. Locker

*Attorney, Agent, or Firm*—C. A. Whealy

[57] ABSTRACT

A distinct cultivar of Chrysanthemum plant named 'Purple Yolima', characterized by its compact and uniformly mounded plant habit; freely branching habit; attractive foliage to floret color contrast; uniform and early flowering; anemone spray-type inflorescences that are about 5.3 cm in diameter; attractive dark purple-colored ray florets and green to dark purple-tipped disc florets; numerous inflorescences per plant; and excellent postproduction longevity with inflorescences and leaves maintaining good substance and color for about four weeks in an interior environment.

2 Drawing Sheets

BACKGROUND OF THE INVENTION

The present invention relates to a new and distinct cultivar of Chrysanthemum plant, botanically known as *Dendranthema grandiflora* and hereinafter referred to by the cultivar name Purple Yolima. The plant is being marketed under the name Purple Lima.

The new Chrysanthemum is a product of a mutation induction breeding program conducted by the inventor in Fort Myers, Fla., and Salinas, Calif. The objective of the program is to create new Chrysanthemum cultivars with desirable inflorescence form and floret colors, good substance, and excellent post-production longevity.

The new Chrysanthemum originated by exposing unrooted cuttings of the Chrysanthemum cultivar Yolima (copening U.S. Plant patent application Ser. No. 09/112,201) to X-ray radiation at a level of 2,000 rads in October, 1994, in Fort Myers, Fla. Following the radiation treatment, the cuttings were rooted and terminal apices were removed (pinched) three times to promote lateral branch development. After lateral branches from the third pinch reached sufficient size, terminal cuttings were harvested, planted and flowered in a controlled environment in Salinas, Calif. The new Chrysanthemum was discovered and selected by the inventor as a single flowering plant within this population in March, 1995. The selection of this plant was based on its desirable inflorescence form and floret colors and excellent post-production longevity.

Asexual reproduction of the new Chrysanthemum by terminal cuttings harvested in a controlled environment in Salinas, Calif., has shown that the unique features of this new Chrysanthemum are stable and reproduced true to type in successive generations.

SUMMARY OF THE INVENTION

The cultivar Purple Yolima has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Purple Yolima'. These characteristics in combination distinguish 'Purple Yolima' as a new and distinct Chrysanthemum:

1. Compact and uniformly mounded plant habit.
2. Freely branching habit, dense plants.
3. Uniform and early flowering.
4. Anemone spray-type inflorescences that are about 5.3 cm in diameter.
5. Attractive dark purple-colored ray florets and green to dark purple-tipped disc florets.
6. Numerous inflorescences per plant.
7. Excellent postproduction longevity with inflorescences and leaves maintaining good substance and color for about four weeks in an interior environment.

Plants of the new Chrysanthemum are similar to plants of the parent cultivar, 'Yolima', and a sibling cultivar, 'Honey Yolima' (U.S. Plant patent application Ser. No. 09/112,202, filed concurrently with this application) in most horticultural characteristics, however plants of the new Chrysanthemum differ from plants of both these cultivars primarily in ray floret color.

The new Chrysanthemum can be compared to the Chrysanthemum cultivar Papillon (disclosed in U.S. Plant Pat. No. 7,435). However in side-by-side comparisons in Salinas, Calif., and Leamington, Ontario, Canada, under commercial practice, plants of the new Chrysanthemum differed from plants of the cultivar Papillon in the following characteristics:

1. Plants of the new Chrysanthemum have larger leaves than plants of the cultivar Papillon.

2. Plants of the new Chrysanthemum have anemone-type inflorescences whereas plants of the cultivar Papillon have single-type inflorescences.

3. Plants of the new Chrysanthemum have larger inflorescences than plants of the cultivar Papillon.

4. Plants of the new Chrysanthemum have longer and more narrow ray florets than plants of the cultivar Papillon.

5. Ray floret color of plants of the new Chrysanthemum is much darker than ray floret color of plants of the cultivar Papillon.

6. Disc florets of plants of the new Chrysanthemum differ in color and have significantly less pollen than plants of the cultivar Papillon.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type.

The photograph at the top of the first sheet comprises a top perspective view of a typical flowering plant of 'Purple Yolima'.

The photograph at the bottom of the first sheet is a close-up view of a typical inflorescences of plants of 'Purple Yolima'.

The photograph at the top of the second sheet is a close-up view of upper (left) and lower (right) surfaces of typical leaves and inflorescences of plants of 'Purple Yolima'.

The photograph at the bottom of the second sheet comprises a side perspective view of typical plants of 'Purple Yolima' (left) and 'Papillon' (right) showing the differences in plant shape, inflorescence type, inflorescence size, and floret colors. Floret and foliage colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown in Salinas, Calif., and Leamington, Ontario, Canada, under greenhouse conditions which approximate those generally used in commercial potted Chrysanthemum production. Four unrooted cuttings were directly stuck in a 15-cm container and pinched once. Measurements and numerical values represent averages of typical flowering plants.

Botanical classification: *Dendranthema grandiflora* cultivar Purple Yolima.

Commercial classification: Anemone spray-type pot chrysanthemum.

Parentage: Induced mutation of *Dendranthema grandiflora* cultivar Yolima.

Propagation:

*Type.*—Terminal tip cuttings.

*Time to rooting.*—Seven to ten days with soil temperatures of 21° C.

*Rooting habit.*—Fine, fibrous and well-branched.

Plant description:

*Appearance.*—Perennial herbaceous anemone spray-type pot Chrysanthemum. Inverted triangle. Stems initially upright, then somewhat spreading giving a uniformly mounded appearance to the plant. Freely branching; about five lateral branches develop after removal of terminal apex (pinching), dense and full plants.

*Plant height.*—Relatively compact, about 22 cm.

*Plant width.*—About 32 cm.

*Foliage description.*—Arrangement: Alternate. Length: About 5.5 cm. Width: About 4 cm. Apex: Mucronate. Base: Attenuate. Margin: Palmately lobed, sinuses between lateral lobes parallel to divergent. Texture: Upper and lower surfaces slightly pubescent. Veins prominent on lower surface. Petiole length: About 1.6 cm. Color: Young foliage upper surface: 147A. Young foliage lower surface: 147B. Mature foliage upper surface: 147A. Mature foliage lower surface: 147B. Venation upper surface: 147A to 147B. Venation lower surface: 147B.

Inflorescence description:

*Appearance.*—Anemone spray-type inflorescence form with oblong-shaped ray florets. Inflorescences borne on terminals above foliage, arising from leaf axils. Disk and ray florets arranged acropetally on a capitulum.

*Flowering response.*—Under natural conditions, plant flowers in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about eight weeks later.

*Postproduction longevity.*—Inflorescences and leaves will maintain good color and substance for about four weeks in an interior environment.

*Quantity of inflorescences.*—About seven inflorescences per terminal with about 35 inflorescences per plant.

*Inflorescence bud.*—Height: About 6.5 mm. Diameter: About 8 mm. Color: 137A.

*Inflorescence size.*—Diameter: About 5.3 cm. Depth (height): About 1.2 cm. Diameter of disc: About 1.9 cm.

*Ray florets.*—Shape: Oblong with very short corolla tube. Aspect: Straight, concave. Length: About 2.5 cm. Width: About 7 mm. Apex: Acute to emarginate. Margin: Entire. Texture: Smooth, glabrous. Number of ray florets per inflorescence: About 24. Color: When opening, upper surface: 64A. When opening, lower surface: 77C. Fully opened, upper surface: 64A. Fully opened, lower surface: Close to 77B.

*Disc florets.*—Shape: Enlarged tubular. Apex: Dentate, flared. Length: About 1 cm. Width: Apex: About 3 mm. Base: About 1 mm. Number of disc florets per inflorescence: About 138. Color: Immature: 143A to 154A. Mature: Apex: 64A to 71A. Mid-section and base: 154A.

*Peduncle.*—Aspect: Flexible, strong, angled about 40° to stem. Length: First peduncle: About 1.1 cm. Fourth peduncle: About 3.2 cm. Texture: Pubescent. Color: Close to 137A.

*Reproductive organs.*—Androecium: Present on disc florets only. Anther color: 7A. Pollen amount: Low to moderate. Pollen color: 9A. Gynoecium: Present on both ray and disc florets.

Disease resistance: No known Chrysanthemum diseases observed to date on plants grown under commercial greenhouse conditions.

Seed production: Seed production has not been observed.

It is claimed:

1. A new and distinct cultivar of Chrysanthemum plant named 'Purple Yolima', as illustrated and described.

* * * * *

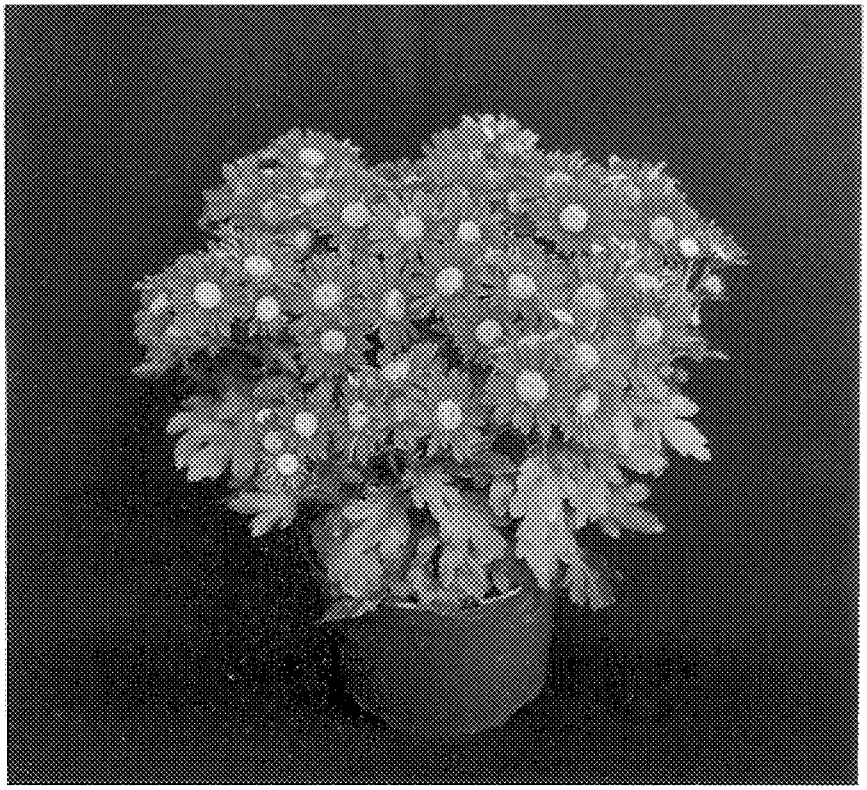
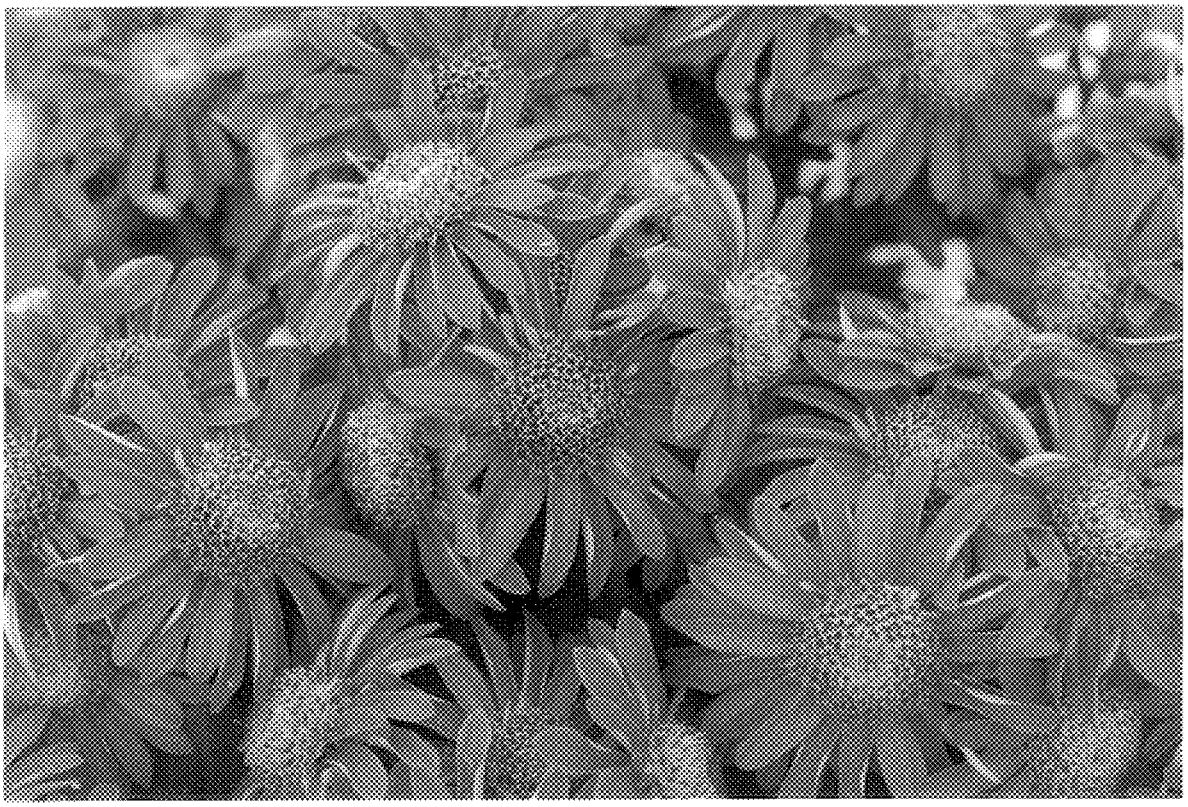

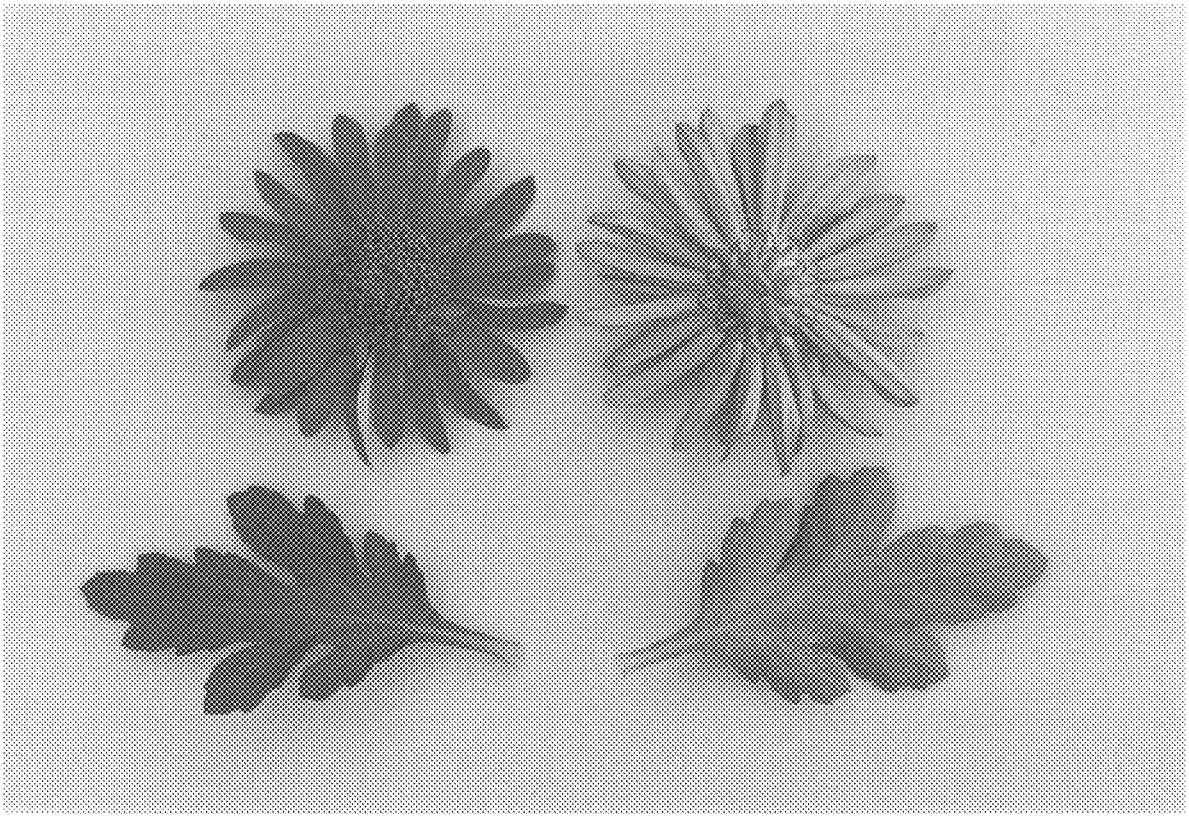
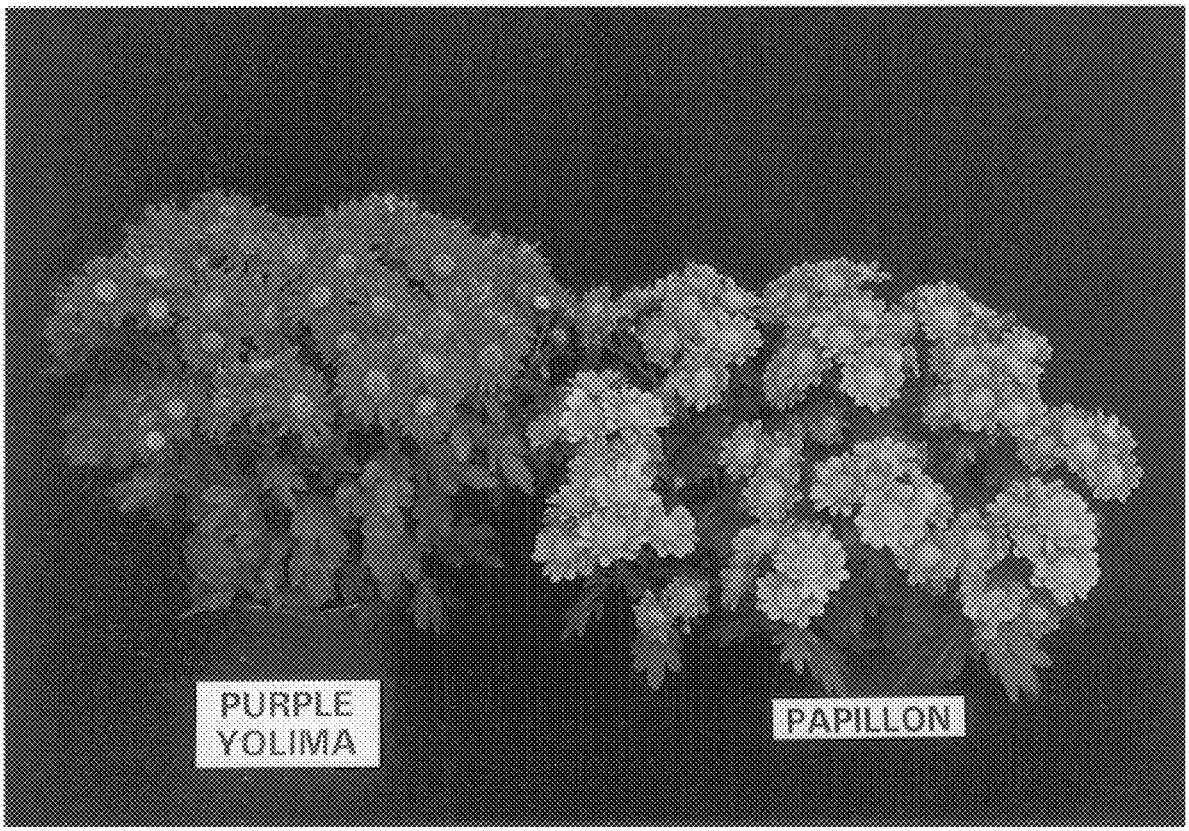
PURPLE
YOLIMA
PAPILLON